(12) United States Patent
Hattori

(10) Patent No.: US 7,900,480 B2
(45) Date of Patent: Mar. 8, 2011

(54) METHOD OF DETERMINING HEATING AMOUNT, METHOD OF FUSION SPLICING, AND FUSION SPLICER

(75) Inventor: Kazunari Hattori, Yokohama (JP)

(73) Assignee: Sumitomo Electric Industries, Ltd., Osaka (JP)

( * ) Notice: Subject to any disclaimer, the term of this patent is extended or adjusted under 35 U.S.C. 154(b) by 941 days.

(21) Appl. No.: 11/317,899

(22) Filed: Dec. 27, 2005

(65) Prior Publication Data

US 2006/0171643 A1 Aug. 3, 2006

(30) Foreign Application Priority Data

Dec. 27, 2004 (JP) ................... 2004-376839

(51) Int. Cl.
*C03B 37/07* (2006.01)
(52) U.S. Cl. .............. 65/377; 65/378; 65/407; 385/96
(58) Field of Classification Search .............. 65/377, 65/378, 407; 385/96
See application file for complete search history.

(56) References Cited

U.S. PATENT DOCUMENTS

| | | | |
|---|---|---|---|
| 5,648,007 A | | 7/1997 | Reslinger et al. |
| 5,785,726 A | * | 7/1998 | Dorfeld et al. ............. 65/134.1 |
| 5,879,426 A | * | 3/1999 | Sanghera et al. ............. 65/405 |
| 5,909,527 A | | 6/1999 | Zheng |
| 6,097,426 A | | 8/2000 | Esmaeili |
| 6,125,225 A | * | 9/2000 | Dianov et al. ............. 385/124 |
| 6,294,760 B1 | | 9/2001 | Inoue et al. |
| 6,370,919 B1 | | 4/2002 | Kossat et al. |
| 6,428,218 B1 | | 8/2002 | Müssig |
| 6,966,708 B2 | * | 11/2005 | Hattori ............. 385/96 |
| 7,699,541 B2 | * | 4/2010 | Ozawa et al. ............. 385/96 |
| 2003/0002827 A1 | | 1/2003 | Ozawa et al. |

FOREIGN PATENT DOCUMENTS

| | | |
|---|---|---|
| EP | 0740172 | 4/1996 |
| EP | 0864889 | 6/1998 |
| EP | 1355177 | 4/2001 |
| JP | 59-160113 A | 9/1984 |
| JP | 02-028605 A | 1/1990 |
| JP | 02-129607 A | 5/1990 |

(Continued)

OTHER PUBLICATIONS

Machine translation of JP 2685152 B, translation created May 13, 2010, pp. 1-3.*

(Continued)

*Primary Examiner* — John Hoffmann
(74) *Attorney, Agent, or Firm* — Global IP Counselors, LLP

(57) ABSTRACT

A method of determining a heating amount adequate for fusion splicing is provided. In the method, the melting state of the end portions of optical fibers can be monitored on a real time basis so that fewer tests need to be performed. A method of fusion splicing and a fusion splicer are also provided. In the method of determining the heating amount, end portions of optical fibers that are placed opposite one another with a predetermined gap therebetween are heat-melted; an image of portions to be heat-melted is observed with an image-capturing device; and a luminance, a light emitting width, or a change in the luminance or the light emitting width is measured. In the method of fusion splicing, optical fibers are heat-melted with the heating amount that is determined using test fibers in advance, or determined using the optical fibers to be fusion spliced.

9 Claims, 4 Drawing Sheets

FOREIGN PATENT DOCUMENTS

| | | |
|---|---|---|
| JP | 05-150132 A | 6/1993 |
| JP | 09-127337 A | 5/1997 |
| JP | 09-138319 A | 5/1997 |
| JP | 2685152 B | 8/1997 |
| JP | 10-274723 A | 10/1998 |
| JP | 10-311926 A | 11/1998 |
| JP | 2002-510064 A | 4/2002 |

OTHER PUBLICATIONS

Notification of Reasons for Rejection in the corresponding Japanese Application No. 2004-376839, dated Jan. 19, 2010.

Notification of Reasons for Rejection in the corresponding Japanese Application No. 2004-376839, dated May 25, 2010.

* cited by examiner

Before heating

After heating

METHOD OF DETERMINING HEATING AMOUNT, METHOD OF FUSION SPLICING, AND FUSION SPLICER

BACKGROUND OF THE INVENTION

1. Field of the Invention

The present invention relates to a method of determining a heating amount that is adequate in fusion splicing optical fibers, a method of fusion splicing that utilizes such determination method, and a fusion splicer for use in such fusion splicing method.

2. Description of the Background Art

In fusion splicing of optical fibers, determination of the heating amount with which end portions to be spliced are heat-melted is vitally important in achieving a low loss connecting. The heating amount that is adequate in fusion splicing of optical fibers varies depending on the type of optical fibers (for example, optical fibers having fluorine in its cladding tend to melt easier), or the environmental factors (temperature, humidity, air pressure, windiness, and so on). Furthermore, while arc discharge is often used in heating optical fibers, it has been known that the number of times the arc discharge electrodes have been used also affects the heating temperature.

Thus, a test arc discharge is normally conducted at the time of fusion splicing in order to adjust and configure the heating amount. A fusion splicer is generally equipped with an image-capturing device and image processing means in order to allow visual observation of the end portions of the optical fibers to be spliced, and it has been known to adjust and configure the heating amount using the image processing means.

Japanese Patent Application Publication No. 5-150132 discloses a method of configuring the heating amount based on the retraction of the end surfaces of the optical fibers caused by the arc discharge heating. In this method, a gap L1 between the end surfaces of the optical fibers before the arc discharge heating and a gap L2 between the end surfaces of the optical fibers after the arc discharge heating are measured (FIGS. 4A and 4B), whether the difference between the gap L1 and the gap L2 (melt back) is within an appropriate range is determined, and the heating amount (arc discharge power) is increased or decreased if the melt back is outside the appropriate range.

Japanese Patent No. 2685152 discloses a method of controlling the arc discharge current based on the area of a glowing portion (light emitting portion) that is generated in the fusion-spliced portions of the optical fibers 19 during the arc discharge heating. In this method, the brightness of the light emitting portion is segmented with the image processing to obtain an area of the light emitting portion and estimate the heating intensity. The result is fed back to the control unit and the arc discharge current is controlled so that the heating temperature is within a predetermined range.

In fusion splicing of optical fibers, an arc discharge test is conducted whenever the type of optical fiber changes, whenever the environmental factors change, and when a long period passes. Thus, reconfiguration of adequate heating amount is conducted relative frequently. Consequently, an arc discharge test is desired to be conducted easily, precisely, and as few times as possible. However, it is practically very difficult to conduct a precise arc discharge test at a construction side such as inside a manhole.

In the method disclosed in the Japanese Patent Application Publication No. 5-150132, at every measurement of the melt back, the arc discharge heating has to be conducted after the fibers have cut, which requires a lot of work. Furthermore, since the melt back is measured after the arc discharge heating is conducted, the heating amount cannot be adjusted or configured on a real time basis. Accordingly, it takes a substantial amount of labor and time to conduct the measurement.

In the case where the heating amount is measured while measuring the area of the light emitting portion that emits light during the arc discharge heating, as in the method disclosed in Japanese Patent No. 2685152, the ends to be spliced tend to become too thin when the heating is excessive. On the other hand, the core misalignment tends to result due to an impact of the fibers being pushed toward one another when the heating is insufficient. In such cases, it is difficult to remedy the problems even by changing the heating amount. Accordingly, the fusion splicing has to be conducted all over again. When the method is performed as an arc discharge test, as in the case of Japanese Patent Application Publication No. 5-150132, the fibers have to be cut and the arc discharge heating has to be performed anew at every measurement. Accordingly, it takes a substantial amount of labor and time to conduct the measurement.

SUMMARY OF THE INVENTION

An object of the present invention is to provide a method of determining the heating amount adequate for fusion splicing of optical fibers, a method of fusion splicing using such determination method, and a fusion splicer for use in such fusion splicing method.

To achieve the objects, the present invention provides a method of determining a heating amount, including: (1) heat-melting end portions of optical fibers that are placed opposite one another with a predetermined gap therebetween; (2) observing with an image capturing device an image of portions to be heat-melted; (3) measuring a luminance, a light emitting width, or a change in the luminance and the light emitting width; and (4) comparing the luminance, the light emitting width, or the change in the luminance or the light emitting width with a predetermined value corresponding to an heating amount adequate for fusion splicing optical fibers.

As another aspect of the present invention, the present invention provides a method of fusion splicing optical fibers, including (1) placing optical fibers opposite one another with a predetermined gap therebetween; (2) heat-melting the optical fibers with the heating amount that is determined in advance using test fibers with the method of determining the heating amount of the present invention; and (3) pushing at least one end portion of end portions of the optical fibers toward the other end portion and fusion splicing, and a method of fusion splicing optical fiber, including 1) placing optical fibers opposite one another with a predetermined gap therebetween; (2) determining a heating amount adequate for fusion splicing the optical fibers with the method of determining the heating amount of the present invention; (3) heat-melting the optical fibers with the heating amount; and (4) pushing at least one end portion of end portions of the optical fibers toward the other end portion and fusion splicing.

As still another aspect of the present invention, the present invention provides a fusion splicer for optical fibers, including (1) arc discharge means for heat-melting end portions of optical fibers that are placed opposite one another with a predetermined gap therebetween; (2) heating amount measuring means for measuring an arc discharge power during arc discharge heating; (3) image observing means for capturing and observing an image of portions of the optical fibers to be heat-melted; (4) image processing means for measuring a luminance or a light emitting width obtained by the image observing means; and (5) a control device for determining a heating amount adequate for fusion splicing, the control device also controlling an arc discharge heating amount.

BRIEF DESCRIPTIONS OF THE DRAWINGS

These and other features, aspects, and advantages of the present invention will become better understood with regard to the following description, appended claims, and accompanying drawings where:

Figure 3A:
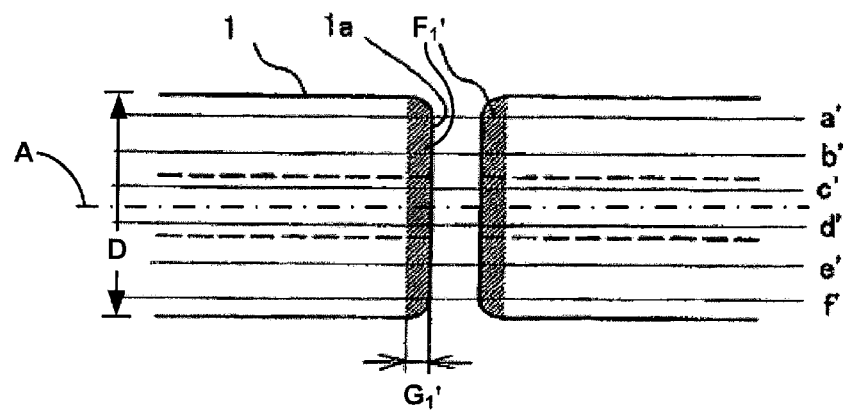
Figure 3B:
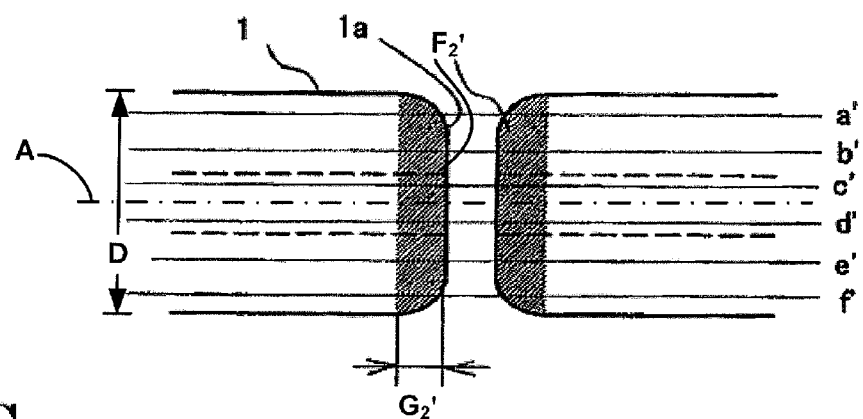
Figure 3C:
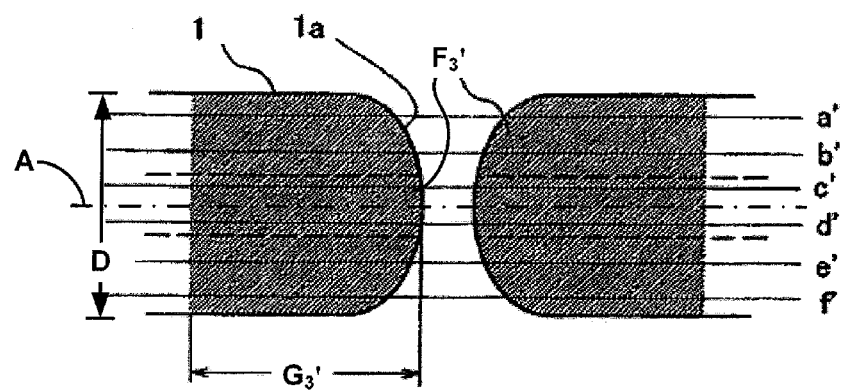
Figure 4A:
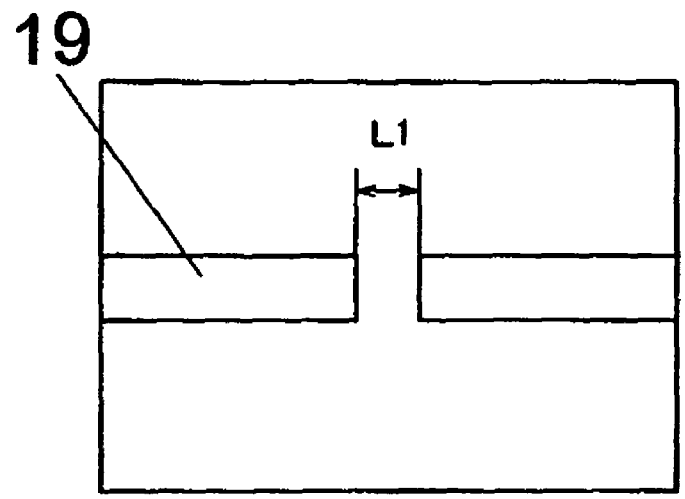
Figure 4B:
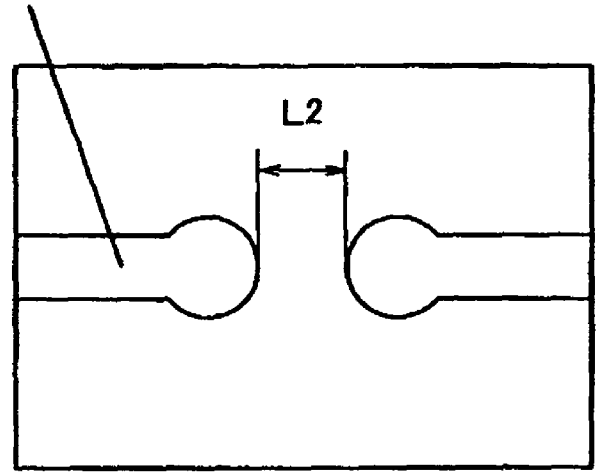

FIGS. 3A-3C are conceptual views illustrating the method of determining the heating amount in accordance with a second embodiment of the present invention, FIG. 3A showing the case where the heating amount is insufficient, FIG. 3B showing the case where the heating amount is adequate, FIG. 3C showing the case where the heating amount is excessive; and FIG. 4 is a conceptual view of conventional methods of detecting the heating amount.

DETAILED DESCRIPTION OF THE INVENTION

Figure 1:
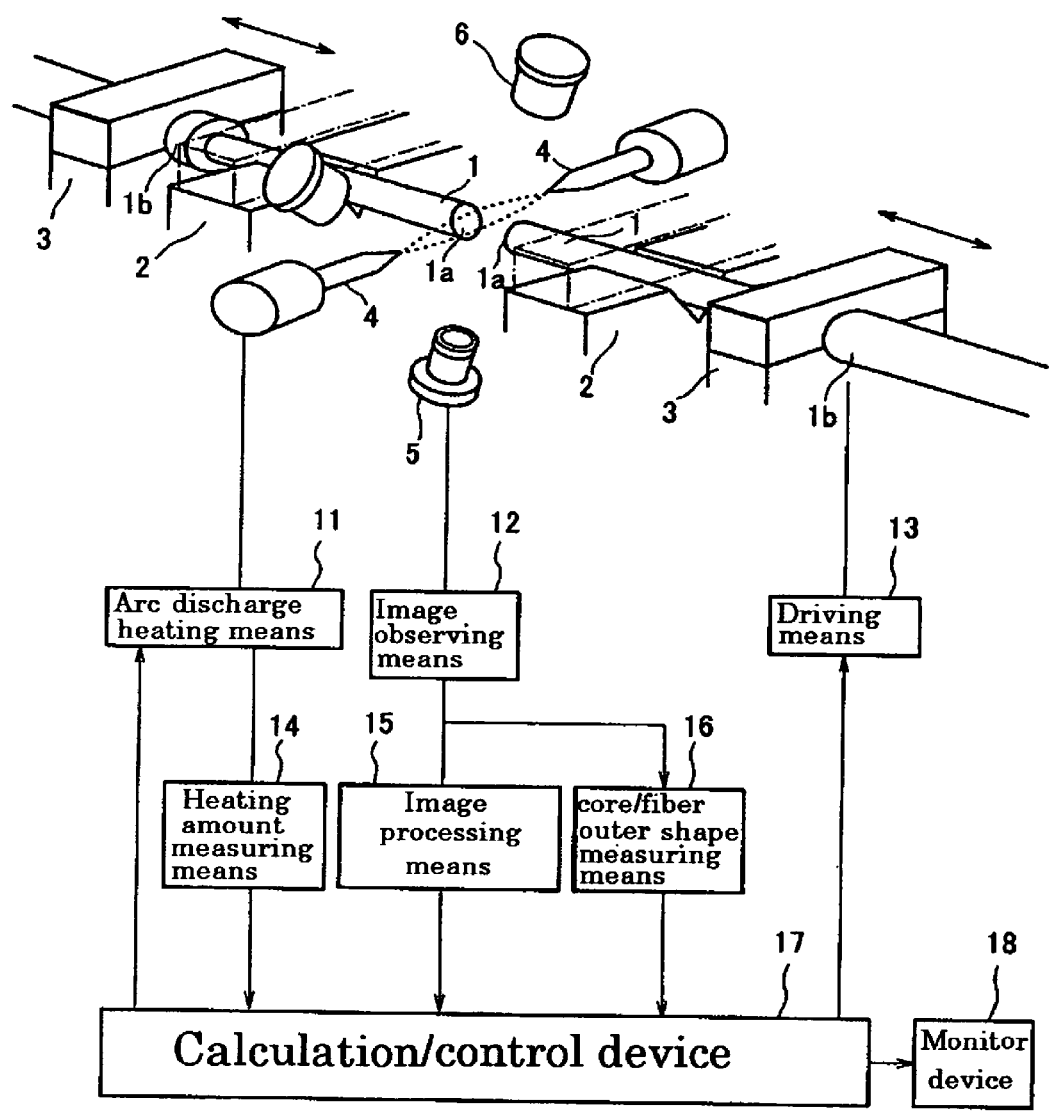
FIG. 1 is a conceptual view illustrating the fusion splicer in accordance with an embodiment of the present invention.

FIG. 1 is a conceptual view of the fusion splicer in accordance with an embodiment of the present invention. A protective coating 1b is removed from the connecting end portions of a pair of optical fibers 1 to be connected. The pair of optical fibers 1 is installed, being held with V-groove clamps 2 with the portion where the glass fibers are exposed and being sandwiched at the protective coating clamps 3 with the end portions of the protective coating 1b. The optical fiber ends 1a are placed opposite each other with the end surfaces being kept apart by a predetermined distance. The state of the optical fiber ends 1a is observed with image observing means 12. The image observing means 12 is, for instance, a microscope, an image capturing camera 5, and a floodlight projector 6.

Core/fiber outer shape measuring means 16 measures the gap between end surfaces of the optical fibers, core offset, and so on. The measurement results are inputted to a control device 17, such that driving means 13 conducts the core alignment and the adjustment of the gap between the end surfaces of the fibers while being displayed in a monitor device 18. Once the end surfaces 1a are set at predetermined positions, arc discharge heating means 11 performs the arc discharge heating. The arc discharge heating means 11 is, for example, arc discharge electrodes 4 that are opposite one another. In the arc discharge heating for the purpose of fusion splicing, the optical fibers 1 are fusion spliced by pressing the fiber end 1a of one of the optical fibers 1 toward the other with the driving means 13.

Figure 2A:
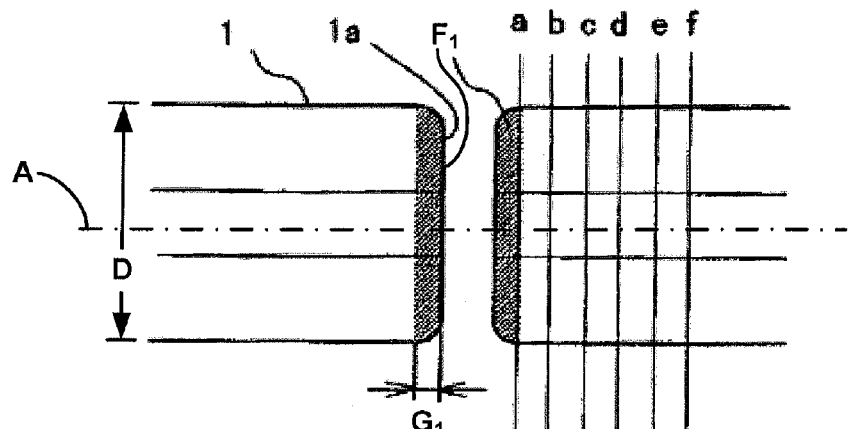
FIGS. 2A-2C are conceptual views illustrating the method of determining the heating amount in accordance with a first embodiment of the present invention, FIG. 2A showing the case where the heating amount is insufficient, FIG. 2B showing the case where the heating amount is adequate, FIG. 2C showing the case where the heating amount is excessive.
Figure 2B:
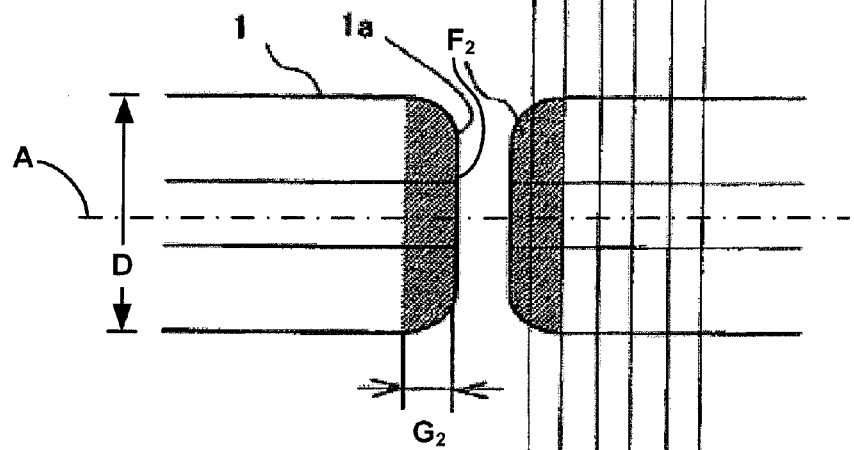
Figure 2C:
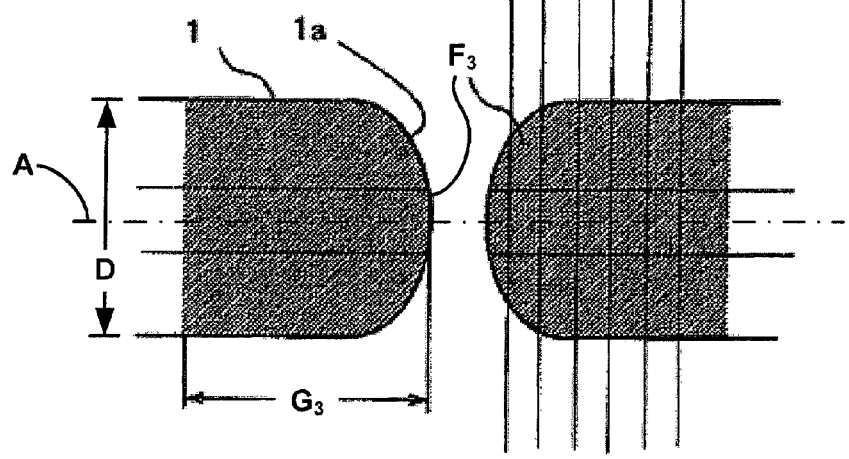

Image data captured by the image observing means 12, which utilizes an image capturing camera 5, are inputted to image processing means 15 so as to be segmented and treated as control data. The image processing means is, for example, a circuit on a substrate. FIGS. 2A-2C are conceptual views illustrating the method of determining the heating amount in accordance with the first embodiment of the present invention, FIG. 2A being the state where the heating amount is insufficient, FIG. 2B being the state where the heating amount is adequate, and FIG. 2C being the state where the heating amount is excessive. As shown in FIGS. 2A-2C, the heating amount (arc discharge power) adequate for the fusion splicing is determined by heating amount measuring means 14 by observing the light emitting state that occurs due to the melting of the fiber ends 1a during the arc discharge heating, and by conducting image processing on the images to create numerical data. The heating amount measuring means 14 is, for example, a microscope and a camera. The light emitting state can also be visually observed through a monitor device 18.

Once the optical fibers are installed in the state shown in FIG. 1, and the arc discharge heating is started after turning off the light of the floodlight projector 6, the optical fibers emit light slightly due to collisions of electrons of the arc discharge current, its outline emitting somewhat stronger light. When the arc discharge current is small, the outline of the optical fibers and the entire fibers are observed in a weak light emitting state. As the arc discharge current increases, only the tip end portions that are opposite each other enter into a fused state, and a region F that has a greater luminance is generated at the tip end portions as shown in FIG. 2A. As indicated in FIG. 2A, the region $F_1$ has a slightly rounded-over outer periphery with an overall width $G_1$. The region $F_1$ is depicted in FIG. 2A as a shaded area that has the width $G_1$ that represents a corresponding axial length of the region $F_1$. The width $G_1$ is measured in a direction that is parallel to an axis A of the optical fiber 1. The rounded-over periphery of the region $F_1$ exhibits an increase in luminance and light emitting state, relative to the untreated remainder of the optical fiber 1. The meaning of the term luminance is well known in the art as being a measurement of candela per unit of measurement, such as meters squared or inches squared. Candela is a well known conventional unit of luminous intensity.

As the arc discharge current increases, the region $F_1$ in FIG. 2A expands in the axial direction to the width $G_2$ of the region $F_2$ depicted in FIG. 2B. The width $G_2$ represents an axial length of the region $F_2$. The region $F_2$ in FIG. 2B has a greater luminance at the tip end portions than the region $F_1$ in FIG. 2A and exhibits an increased amount of luminance relative to the region $F_1$ in FIG. 2A. As the arc discharge current increases further, substantially broad areas covering most of the end portions of the optical fibers become the region $F_3$ having an even greater luminance and a width $G_3$, as shown in FIG. 2C. When the heating is excessive, it is necessary to weaken the arc discharge current by, for example, stopping the arc discharge right away, or by retracting the fibers temporarily and retrying the fusion later. Furthermore, the arc discharge heating can be carried out intermittently with the arc discharge for a short period.

By observing the light emitting state of end portions of the optical fibers from the time at which the arc discharge heating is started, it is possible to detect the arc discharge power that corresponds to the state of the heat-melting. For example, the light emitting state shown in FIG. 2A of the region $F_1$ with the width $G_1$, the melting is insufficient for fusion splicing. When the pushing of the optical fibers (normally, one of the optical fibers is pushed toward the other) is performed at the light emitting state of the region $F_2$, with the width $G_2$, shown in FIG. 2B (the width $G_2$ can be greater than 20µm and smaller than 100µm, for instance between 10-30µm), the fusion splicing can be performed in a favorable manner. In the light emitting state of the region $F_3$ with the width $G_3$ shown in FIG. 2C (greater than 100µm), the arc discharge power is excessive. If the pushing of the optical fibers is performed in this state, the fusion-spliced portion will become deformed, and there will be a large splicing loss. In this manner, by observing the light emitting state of the end portions of the optical fibers, the light emitting state most adequate for fusion splicing can be determined, such that the arc discharge power at that state can be detected. By performing the fusion splicing using the detected value as a configuration value, it is possible to perform the fusion splicing without causing much loss.

To determine the light emitting sate corresponding to the most adequate melting state for fusion splicing, there are a method in which the strength of the luminance at a predetermined position in the observation image is determined, a method in which an area that has the luminance equal to or greater than a predetermined level of luminance is measured, and a method in which a change in these variables is measured. In order to actually perform these methods, the optical fibers to be connected, or optical fibers that are of the same type as the optical fiber to be connected and are to be used for the arc discharge test purpose, are installed in the fusion splicer as shown in FIG. 1. The tip end portions of the optical fibers are heated with the arc discharge heating means 11 as the arc discharge power is increased gradually. Images of the light emitting portions of the optical fibers are captured at predetermined timings, and the images thus captured are retrieved successively by the image observing means 12.

Next, the images thus captured are inputted to the image processing means 15. The images are scanned in a direction that intersects the optical fiber at positions (a-f), which are at predetermined distances from the tip end. The luminance is measured at the scanning positions (a-f). Any desired number of the scanning positions can be set at any desired interval (for example, 10 μm) therebetween in the axial direction. The luminance is measured by setting a threshold value and measuring the luminance greater than a predetermined level.

If the luminance measured at the predetermined position (for example, the scanning line b) from the tip end of the fiber is below the predetermined level, the melting is insufficient. Thus, the arc discharge current is increased and the heating is continued. The measurement continues to be performed on a real time basis. When the luminance at the predetermined position (for example, the scanning line b) reaches the predetermined level, the arc discharge power at the time is measured and determined as the most adequate value. In this manner, by increasing the arc discharge power gradually and observing the portion that is being heat-melted on a real time basis, it is possible to configure the heating amount adequate for fusion slicing quickly. Furthermore, it is possible to conduct the arc discharge test as a part of the fusion splicing process in place of conducting the test separated from the splicing process. As a result, it is possible to prevent problems that occur due to failure to set the heating configurations.

The arc discharge heating can be stopped and the measurement can be ended at the point where the luminance reaches the predetermined level. Alternatively, it is also possible to measure the arc discharge power at a luminance where the arc discharge power is further increased. Furthermore, by measuring the state of changes in the images, in other words the change in the luminance at a predetermined position over time, it is possible to measure the arc discharge power at the time when such change reaches a predetermined value. The fusion splicer for the method of the present embodiment merely utilizes the conventional arc discharge heating means and image observing means, and merely modifies the image processing method and the control method. Thus, the method of the present embodiment can be implemented without having to increase the cost.

As shown in FIGS. 2A-2C, the regions $F_1$, $F_2$ and $F_3$ where the luminance is strong varies depending on the arc discharge power. Thus, it is possible to measure the arc discharge power most adequate for fusion splicing by measuring the width, for example, the widths $G_1$, $G_2$ and $G_3$ (the width from the tip end of the fiber) of the regions $F_1$, $F_2$ and $F_3$ and determine which of the regions $F_1$, $F_2$ and $F_3$ have a luminance greater than a predetermined and desirable level. The light emitting widths $G_1$, $G_2$ and $G_3$ can be measured by scanning the fiber at a plurality positions that are set at predetermine distances from the tip end of the fiber in a direction that intersects the axis of the fiber, and detecting the luminance that is greater than a predetermined level at these predetermined scanning positions. The outer diameter of the optical fiber is normally 125μm. Further, as mentioned above, the optimal light emitting width $G_2$ for the present invention is preferably greater than 20μm and smaller than 100μm, and more preferably between 10-30μm. Hence, for an optical fiber having an outer diameter of 125μm, the preferred light emitting width $G_2$ is between 16% and 80% of the outer diameter of the optical fibers and more preferably between 8% and 24% of the outer diameter of the optical fibers.

If the measured light emitting width $G_1$ from the tip of the fiber is small as shown in FIG. 2A, the melting is insufficient. Thus, the arc discharge current is increased, and the heating is performed continuously. Measurement of the light emitting width $G_1$ is performed on a real time basis. When the light emitting width reaches the predetermined light emitting width $G_2$ (most adequate value) shown in FIG. 2B, the arc discharge power at that point is measured. At this point, the arc discharge heating can be stopped and the measurement can be ended. Alternatively, it is also possible to measure the arc discharge power at the luminance when the arc discharge power is further increased. Furthermore, by capturing the images at predetermined timings, it is possible to measure the state of changes in the images, in other words the change in the light emitting width over time, and measure the arc discharge power may be measured at the time when such change reaches a predetermined value.

FIGS. 3A-3C are conceptual views illustrating the method of determining the heating amount in accordance with the second embodiment of the present invention, FIG. 3A being the state where the heating amount is insufficient of a region $F_1'$ with a width $G_1'$, FIG. 3B being the state where the heating amount is adequate of a region $F_2'$ with a width $G_2'$, and FIG. 3C being the state where the heating amount is excessive of a region $F_3'$ with a width $G_3'$. The luminance can be measured either by scanning the image in a direction that intersects the axis of the fiber as in the first embodiment, or by scanning the image in a direction that is parallel to the axis A of the fiber as in the second embodiment. Since the second embodiment is the same as the first embodiment except for the direction of scanning, detailed explanation of the second embodiment is omitted herein. Since the outer diameter of the optical fiber is normally 125μm, when the scanning positions (a'—f') are set at the interval of 10μm, as in the case of FIGS. 2A-2C, it is possible to conduct the measurement at ten lines. Since the scanning is performed in a direction that intersects with the ends 1a of both of the optical fibers 1, it is possible to easily capture the changes as shown in FIGS. 3A-3C, and thereby a more precise measurement is performed.

Once the arc discharge power most adequate for fusion splicing is determined with the method described above, the arc discharge heating at the time of fusion splicing of the optical fibers is controlled using the determined arc discharge power as the configured value. This detection of the arc discharge power can be conducted as part of the image observing process that is conducted at the time of arc discharge test. Furthermore, since the melting state of the fibers as a result of the arc discharge heating can be processed on a real time basis, and the arc discharge power at each state can be detected one by one, it is possible to precisely measure the arc discharge power most adequate for fusion splicing with few arc discharge tests.

The method of determining the heating amount described above can be performed every time the fusion splicing of optical fibers is to be performed. This is more advantageous than the case where an arc discharge test is performed in advance particularly when, for instance, the number of fusion splicing to be performed is small, when there are many types of optical fibers, and when the splicing environment changes easily. It is also possible to prevent an unsuccessful connecting when the arc discharge test failed to be performed.

At the time of fusion splicing, before the arc discharge heating is started prior to the pushing operation of the fibers, there is normally a waiting period called preliminary arc discharge period, during which the end surfaces of the fibers are shaped. This period is approximately 0.1-0.3 seconds. By detecting the above described arc discharge power most adequate for the fusion splicing on a real time basis during this preliminary arc discharge period, it is possible to implement the above described method without necessitating the fusion splicing to take any additional time.

While this invention has been described in connection with what is presently considered to be the most practical and preferred embodiments, the invention is not limited to the disclosed embodiments, but on the contrary, is intended to cover various modifications and equivalent arrangements included within the spirit and scope of the appended claims.

For instance, the present invention can be implemented in the same manner in a multi-coaxial optical fiber in which a plurality of optical fibers is arranged in one line in parallel. In this case, at least one optical fiber is selected among the multi-coaxial optical fibers, and the arc discharge power most adequate for the entire multi-coaxial optical fiber is detected while observing the melting state of the selected optical fiber.

The entire disclosure of Japanese Patent Application No. 2004-376839 filed on Dec. 27, 2004 including specification, claims, drawings and summary are incorporated herein by reference in its entirety.

What is claimed is:

1. A method of determining an amount of heating adequate for fusion splicing optical fibers, the method comprising the steps of:
   (1) heating of end portions of optical fibers that are placed opposite one another with a predetermined gap there between;
   (2) observing the end portions of the optical fibers with an image capturing device to capture an image of the end portions of the optical fibers being heated;
   (3) measuring a light emitting width of one of the end portions of the optical fibers being heated, the light emitting width corresponding to changes in a light emitting state of the end portions of the optical fibers that occurs due to heating, the light emitting width being measured along a direction that is parallel to an axis of the one of the optical fibers;
   (4) comparing the measured light emitting width with a value, the value corresponding to the end portions of the optical fibers being in a state adequate for fusion splicing; and
   (5) determining the amount of the heating provided to the end portions of the optical fibers once the measuring indicates that the light emitting width has reached the value.

2. The method according to claim 1, wherein the comparing of the measured light emitting width with the value is such that, with an outer diameter of the optical fibers being 125 μm, the value is equal to an axial length of the end portion of the optical fiber that is greater than 16% of the outer diameter of the optical fibers and less than 80% of the outer diameter of the optical fibers.

3. The method according to claim 1, wherein the comparing of the measured light emitting width with the predetermined level of luminance is such that, with an outer diameter of the optical fibers being 125 μm, the value is equal to an axial length of the end portion of the optical fiber greater than 8% of the outer diameter of the optical fibers and less than 24% of the outer diameter of the optical fibers.

4. The method according to claim 1, wherein the comparing of the measured light emitting width is performed such that when the measured light emitting width has reached the value, the heating of the end portions is stopped.

5. The method according to claim 1, further comprising controlling the heating of the end portions of the optical fibers such that:
   in response to the light emitting width being less than the value, heating is continued; and
   in response to the light emitting width reaching the value, heating is stopped.

6. The method according to claim 1, wherein the heating of the end portions of the optical fibers is provided by arc discharge power.

7. A method of fusion splicing optical fibers, the method comprising determining an amount of heating necessary for adequate fusing of end portions of optical fibers and a splicing operation, wherein
   the determining of the amount of heating necessary for adequate fusing of end portions of optical fibers comprises:
      heating end portions of test optical fibers that are placed opposite one another with a predetermined gap therebetween;
      observing the end portions of the test optical fibers with an image capturing device to capture an image of the end portions of the test optical fibers during the heating of the end portions of the test optical fibers;
      measuring a light emitting width of one of the end portions of the test optical fibers being heated, the light emitting width corresponding to changes in a light emitting state of the test optical fibers that occurs due to heating of the fiber ends of the test optical fibers, the light emitting width being measured along a direction that is parallel to an axis of the test optical fibers;
      comparing measured the light emitting width with a value, the value corresponding to the end portions of the test optical fibers being in a state adequate for fusion splicing; and
      determining the amount of the heating provided to the end portions of the test optical fibers once the light emitting width has reached the value; and
   the splicing operation comprising:
      placing first and second optical fibers opposite one another with a predetermined gap therebetween;
      heating end portions of the first and second optical fibers with the amount of the heating determined in steps of the determining the amount of the heating; and pushing an end portion of one of the first and second optical fibers toward the other end portion to fusion splice the end portions of the first and second optical fibers together.

8. The method according to claim 7, wherein the heating of the end portions of the test optical fibers is provided by arc discharge power.

9. A method of fusion splicing optical fibers, comprising the steps of:

heating end portions of optical fibers that are placed opposite one another with a predetermined gap therebetween;

observing the end portions of the optical fibers with an image capturing device to capture an image of the end portions of the optical fibers;

measuring a light emitting width of one of the end portions of the optical fibers, the light emitting width corresponding to changes in a light emitting state of the optical fibers that occurs due to heating of the fiber ends, the light emitting width being measured along a direction parallel to an axial length of the optical fibers;

comparing the measured light emitting width with a value, the value corresponding to the end portions of the optical fibers being in a state adequate for fusion splicing; and determining the amount of the heating provided to the end portion of the optical fibers once the light emitting width reaches the value;

heating end portions of the optical fibers with arc discharge power corresponding to the amount of the heating determined in the step of determining of the amount of the heating; and pushing at least one end portion of one of the optical fibers toward the other end portion to fusion splice the optical fibers together.

* * * * *